(12) United States Patent
Silk et al.

(10) Patent No.: US 8,029,814 B2
(45) Date of Patent: Oct. 4, 2011

(54) **MALE PRODUCED PHEROMONE IN *TETROPIUM FUSCUM* (F.) AND *TETROPIUM CINNAMOPTERUM* (KIRBY) (COLEOPTERA: CERAMBYCIDAE)**

(75) Inventors: Peter Silk, Fredericton (CA); Jon Sweeney, Fredericton (CA)

(73) Assignee: Her Majesty the Queen in Right of Canada as represented by the Minister of Natural Resources, Canada, Canadian Forest Service, Ottawa (CA)

( * ) Notice: Subject to any disclaimer, the term of this patent is extended or adjusted under 35 U.S.C. 154(b) by 414 days.

(21) Appl. No.: 12/237,903

(22) Filed: Sep. 25, 2008

(65) Prior Publication Data

US 2009/0092577 A1    Apr. 9, 2009

Related U.S. Application Data

(60) Provisional application No. 60/960,447, filed on Sep. 26, 2007.

(51) Int. Cl.
*A01N 25/02* (2006.01)
(52) U.S. Cl. .......................................... 424/405; 43/107
(58) Field of Classification Search ................... 424/405; 43/107
See application file for complete search history.

(56) References Cited

U.S. PATENT DOCUMENTS 6,607,712 B2 *   8/2003   Majeed et al. .................. 424/58

FOREIGN PATENT DOCUMENTS

WO    WO-01/85120 A1 * 11/2001

OTHER PUBLICATIONS

Silk et al. (Evidence for a male-produced pheromone in *Tetropium fuscum* (F.) and *Tetropium cinnamopterum* (Kirby) (Coleoptera: Cerambycidae, Naturwissenschaften, vol. 94, p. 697-701, Published Apr. 12, 2007).*

* cited by examiner

*Primary Examiner* — Karlheinz R Skowronek
*Assistant Examiner* — Ali Soroush
(74) *Attorney, Agent, or Firm* — Michael R. Williams

(57) ABSTRACT

Described herein is (E)-6,10-dimethyl-5,9-undecadien-2-ol (geranyl acetol), termed here fuscumol, which has been identified as a male-produced pheromone emitted by *Tetropium fuscum* (F.) and *Tetropium cinnamopterum*. Also described are novel derivatives thereof e.g. esters, methods for the synthesis thereof and to a composition comprising fuscumol plus host volatiles e.g. a synthetic blend of monoterpenes plus ethanol, for attracting male and female *T. fuscum* and female *T. cinnamopterum*.

8 Claims, 14 Drawing Sheets a) EI-mass spectrum of the Natural Pheromone, P b) EI-mass spectrum of the PCC Oxidation Product of Natural P a. *Tetropium fuscum* catch, NS 2006 b. *T. cinnamopterum* catch, NS 2006

SCHEME 1

SCHEME 2

SCHEME 3

SCHEME 4

SCHEME 5

Tetropium fuscum Release rate expt 1, 2007

23 May - 27 June

Fig. 9

MALE PRODUCED PHEROMONE IN *TETROPIUM FUSCUM* (F.) AND *TETROPIUM CINNAMOPTERUM* (KIRBY) (COLEOPTERA: CERAMBYCIDAE)

PRIOR APPLICATION INFORMATION

This application claims the benefit of U.S. Provisional Patent Application 60/960,447, filed Sep. 26, 2007.

BACKGROUND OF THE INVENTION

Described herein is (E)-6,10-dimethyl-5,9-undecadien-2-ol (geranyl acetol), termed here fuscumol, which has been identified as a male-produced pheromone emitted by *Tetropium fuscum* (F.) and *Tetropium cinnamopterum*. Also described are novel derivatives thereof e.g. esters, methods for the synthesis thereof and to a composition comprising fuscumol plus host volatiles e.g. a synthetic blend of monoterpenes plus ethanol, for attracting male and female *T. fuscum* and female *T. cinnamopterum*.

We have been developing tools for detection of the brown spruce longhorn beetle, *Tetropium fuscum* (F.) (Coleoptera: Cerambycidae: Spondylidinae), a Palearctic species inadvertently introduced to Canada and discovered near the port of Halifax, Nova Scotia, Canada, in 1999 (Smith and Hurley 2000)[1]. In Europe, *T. fuscum* breeds primarily in moribund Norway spruce, *Picea abies* (L.) Karst. In Nova Scotia, it is infesting red spruce, *P. rubens* Sarg., white spruce, *P. glauca* (Moench) Voss, black spruce, *P. mariana* (Mill.) B.S.P., and Norway spruce (Smith and Humble 2000)[2]. Many cerambycids are attracted to conifer volatiles (Allison et al. 2004)[5]. A synthetic blend of monoterpenes simulating spruce cortical volatiles plus ethanol is attractive to *T. fuscum*, *T. cinnamopterum* Kirby and *T. castaneum* (L.) (Sweeney et al. 2004, 2006)[3,4]. However, a pheromone-based attractant should detect *T. fuscum* at lower population densities and be more species specific than host volatiles. In cerambycids studied to date, long-range pheromones tend to be short-chain (6-10 carbons) hydroxy ketones or diols released by males that elicit attraction in either both sexes or females only (Allison et al. 2004[5]; Lacey et al. 2004[6].

SUMMARY OF THE INVENTION

According to one aspect of the invention, a composition comprising as active ingredient (E)-6,10-dimethyl-5,9-undecadien-2-ol and conifer volatiles, is provided. In one embodiment, the active ingredient is in the S-chiral form and in another embodiment in the racemic S/R-form. In other embodiments, the conifer volaties include these disclosed in Allison et al. 2005[5], and in Sweeney et al 2004[3], 2006[4], the disclosures of which are incorporated herein by reference. Specifically, as will be appreciated by one of skill in the art, 'conifer volatiles' or 'host volatiles' or 'spruce volatiles' for example refer to volatiles from conifers which are well-known in the art. Typically, the volatiles comprise monoterpenes and sesquiterpenes, for example, α-pinene, β-pinene, 3-carene, limonene and α-terpinoline. As will be appreciated by one of skill in the art, the actual percentages or ratios of these compounds in the volatiles of a given conifer will vary somewhat depending on many factors including but by no means limited to growth conditions, and age and condition of tree. Accordingly, as used herein, 'conifer volatiles', 'host volatiles' or 'spruce volatiles' refers to for example one or more of the compounds listed above, more preferably to a mixture of two or more of the compounds listed above. In preferred embodiments, the term 'conifer volatiles' refers to a natural or synthetic mixture which mimics or approximates or reproduces the compound(s) volatized by a conifer. As discussed herein, such mixtures are available commercially or may be quickly and easily produced by mixing specific chemicals, as will be readily apparent to one of skill in the art.

According to another aspect of the invention ester derivatives of (E)-6,10-dimethyl-5,9-undecadien-2-ol are provided as novel compounds.

According to another aspect of the invention, a method of attracting insects from the taxonomic groups *Tetropium castaneum*, *Tetropium fuscum* and *Tetropium cinnamopterum* is provided, comprising applying to a target, an effective amount of the above composition. The target may be for example the insect habitat or a trap or other similar device or structure.

According to yet another aspect of the invention, there is provided synthetic (E)-6,10-dimethyl-5,9-undecadien-2-ol and ester derivatives thereof as well as methods for producing same. As discussed herein, synthesis of racemic and optically enriched S-fuscumol was undertaken via the following approaches:

(a) use of alkyl-CBS-oxazaborilidine catalysts to effect asymmetric reductions of prochiral ketones using borane adducts as reducing agents; other reducing agents of this type will also be used; high "ee's" are the expected outcome.

(b) Chiral synthetic approaches beginning with chirally pure R- and S-lactate esters and copper catalyzed Grignard coupling to chiral lactyl alcohol tosylates.

(c) Kinetic resolution of racemic secondary alcohols using a lipase (e.g. Novozyme 425) followed by chromatographic resolution and purification to obtain both R- and S-fuscumol simultaneously.

(d) Production of racemic fuscumol by borohydride or LAH reduction of geranyl acetone, shown in FIG. 5 and discussed below.

It is noted that the molecule of 6,10-dimethyl-5,9-undecadien-2-ol (an "incomplete" systematic name, in that it does not reflect the stereochemistry of the compound) is a compound with two double bonds (positioned at carbon atoms C5 and C9, the numbering starting at the end closer to the hydroxy group) and an asymmetric carbon atom C2 (the one to which the hydroxy group is attached). The substitution patterns at the double bonds of the molecule and its C2 carbon atom allow for two possible stereoisomers at each of C2, C5 carbon atoms, to a total of four stereoisomers possible for that compound. Of those, only one is the fuscumol produced by *Tetropium* insects and a complete systematic name of this molecule reflecting its unique stereochemistry is (2S, 5E)-6,10-dimethyl-5,9-undecadien-2-ol, where symbols 2S, 5E at the beginning of the name indicate the configuration at carbon atoms C2, C5 and C9, respectively.

According to another aspect of the invention, there is provided a method for synthesizing (E)-6,10-dimethyl-5,9-undecadien-2-ol comprising:

dissolving E-(trans)-geranyl acetone in anhydrous tetrahydrofuran;

cooling the mixture to 0° C. on ice;

adding lithium aluminum hydride slowly while stirring the mixture;

quenching the reaction by adding water drop wise;

extracting the mixture with diethyl ether; and drying the extract over magnesium sulfate.

BRIEF DESCRIPTION OF THE DRAWINGS

FIGS. 9-12 show capture of *T. fuscum* and *T. cinnamopterum* in cross-vane traps baited with different release rates of racemic fuscumol, with and without host volatiles: MAX+SB+E=racemic fuscumol max release rate+spruce blend+ethanol; HI+SB+E=racemic fuscumol high release rate+spruce blend+ethanol; MED+SB+E=racemic fuscumol medium release rate+spruce blend+ethanol=(standard lure); LO+SB+E=racemic fuscumol low release rate+spruce blend+ethanol; SB+E=spruce blend+ethanol; MAX=racemic fuscumol max release rate HI=racemic fuscumol high release rate; MED=racemic fuscumol medium release rate; LO=racemic fuscumol low release rate; and unbaited FIG. 13 Mean catch of *T. castaneum* in traps baited with low (1 mg/d), medium (4 mg/d) or high (32 mg/d) of racemic fuscumol plus spruce volatile (SB) and ethanol (E) lures. FT="fuscumate" or geranyl acetate, which did not boost catch compared to SB+E.

DETAILED DESCRIPTION OF THE INVENTION

Figure 1:
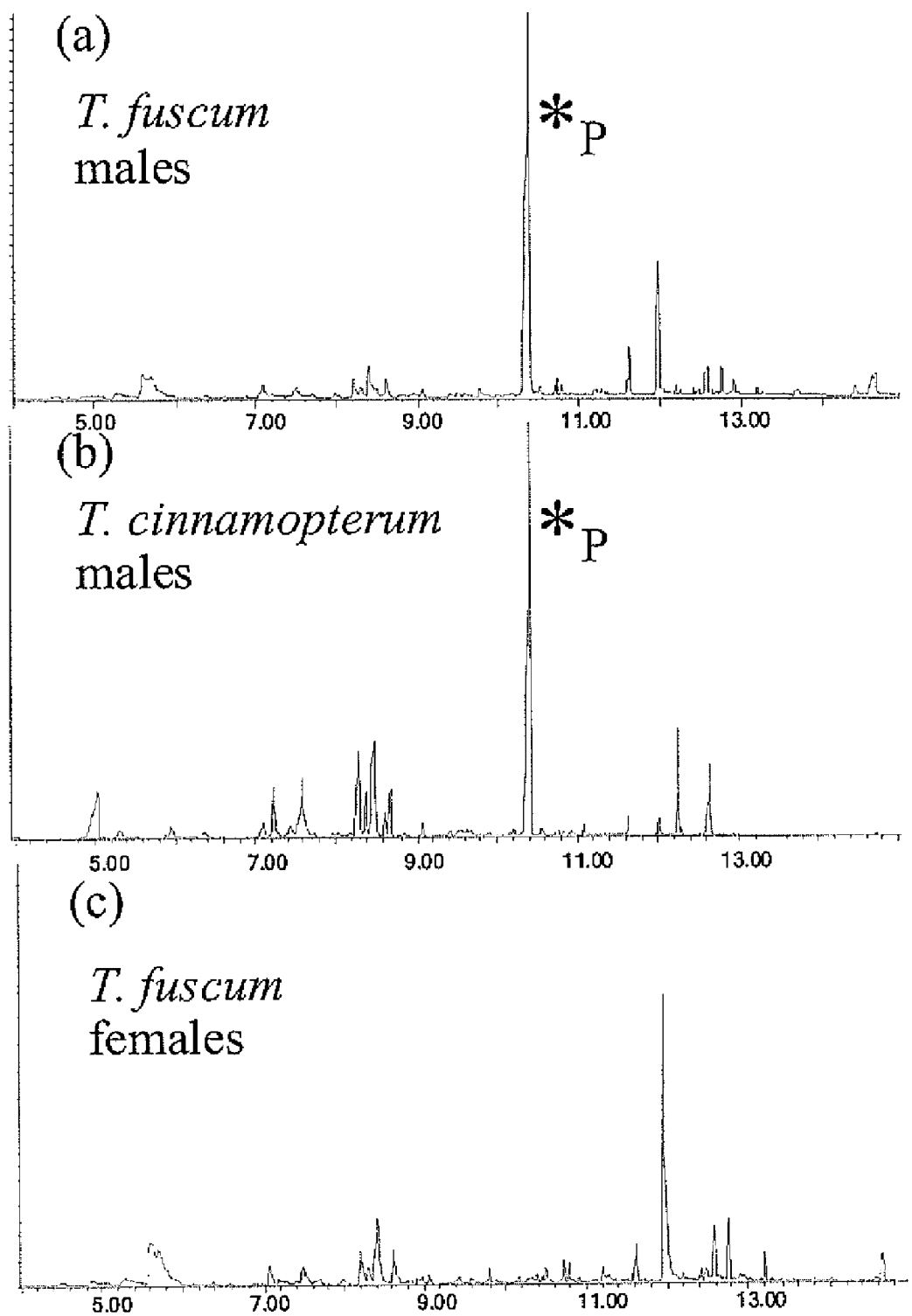
FIG. 1. GC/MS analysis of volatiles collected from *T. fuscum* males (a) *T. cinnamopterum* males (b) and *T. fuscum* females (c) *P is fuscumol. X-axis, time (min); Y-axis, total ion current.

Described herein is the first evidence of a pheromone in the Spondylidinae subfamily and is the first of its structural motif described from the Cerambycidae. The male-produced compound (E)-6,10-dimethyl-5,9-undecadien-2-ol, or "fuscumol," was observed in both *T. fuscum* and *T. cinnamopterum*. We presume the main role of fuscumol is as a sex pheromone for attraction of females to males and that response of male *T. fuscum* increases probability of encountering females. Lack of response by male *T. cinnamopterum* suggests that fuscumol may not be its only sex pheromone component. The lack of significant catch of either species in traps baited with fuscumol alone suggests that simultaneous host volatile stimulation may be necessary to elicit response to the pheromone (Landolt and Phillips 1997)[8], that the release rate of fuscumol was not optimal, or that fuscumol is not the only pheromone component. Thus, it is shown herein that although the pheromone, either purified or synthesized, fails to act as an attractant on its own but surprisingly produces a much more effective attractant composition when combined with a source of conifer volatiles and ethanol.

According to one aspect of the invention, a composition comprising as active ingredient (E)-6,10-dimethyl-5,9-undecadien-2-ol and conifer volatiles, is provided. In one embodiment, the active ingredient is in the S-chiral form and in another embodiment in the racemic S/R-form. In other embodiments, the conifer volaties include these disclosed in Allison et al. 2004[5], and in Sweeney et al 2004[3], 2006[4], the disclosures of which are incorporated herein by reference. Specifically, as will be appreciated by one of skill in the art, 'conifer volatiles' or 'host volatiles' or 'spruce volatiles' for example refer to volatiles from conifers which are well-known in the art. Typically, the volatiles comprise monoterpenes and sesquiterpenes, for example, α-pinene, β-pinene, 3-carene, limonene and α-terpinoline. As will be appreciated by one of skill in the art, the actual percentages or ratios of these compounds in the volatiles of a given conifer will vary somewhat depending on many factors including but by no means limited to growth conditions, and age and condition of tree. Accordingly, as used herein, 'conifer volatiles', 'host volatiles' or 'spruce volatiles' refers to for example one or more of the compounds listed above, more preferably to a mixture of two or more of the compounds listed above. In preferred embodiments, the term 'conifer volatiles' refers to a natural or synthetic mixture which mimics or approximates or reproduces the compound(s) volatized by a conifer. As discussed herein, such mixtures are available commercially or may be quickly and easily produced by mixing specific chemicals, as will be readily apparent to one of skill in the art.

Thus, as discussed herein, the composition acts as an attractant for *Tetropium castaneum*, *Tetropium fuscum* and *Tetropium cinnamopterum*. As such, in one embodiment of the invention, there is provided a *Tetropium* attractant comprising a source of conifer volatiles and synthetic or purified (E)-6,10-dimethyl-5,9-undecadien-2-ol or derivatives thereof. As discussed herein, the S-chiral form is the active form; however, the presence of the R-chiral form does not inhibit or hinder the activity of the S-chiral form, meaning that racemic mixtures of (E)-6,10-dimethyl-5,9-undecadien-2-ol may be used in the attractant.

Figure 11:
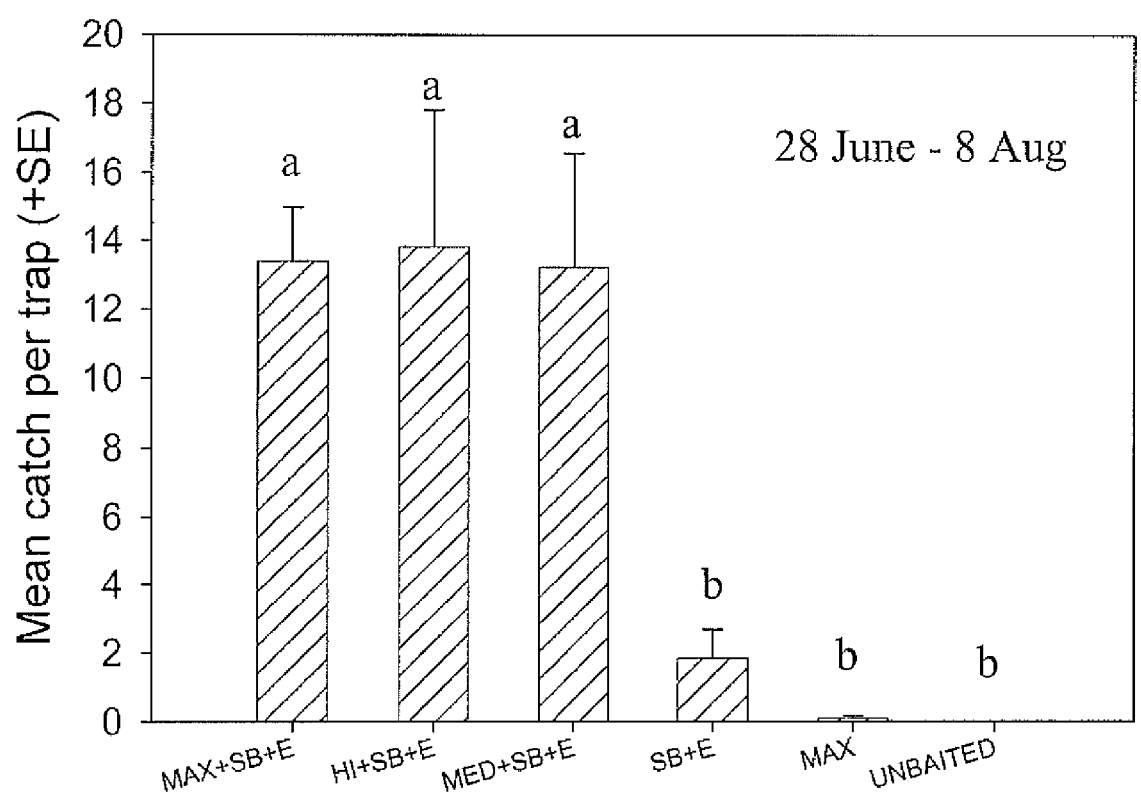
Figure 12:
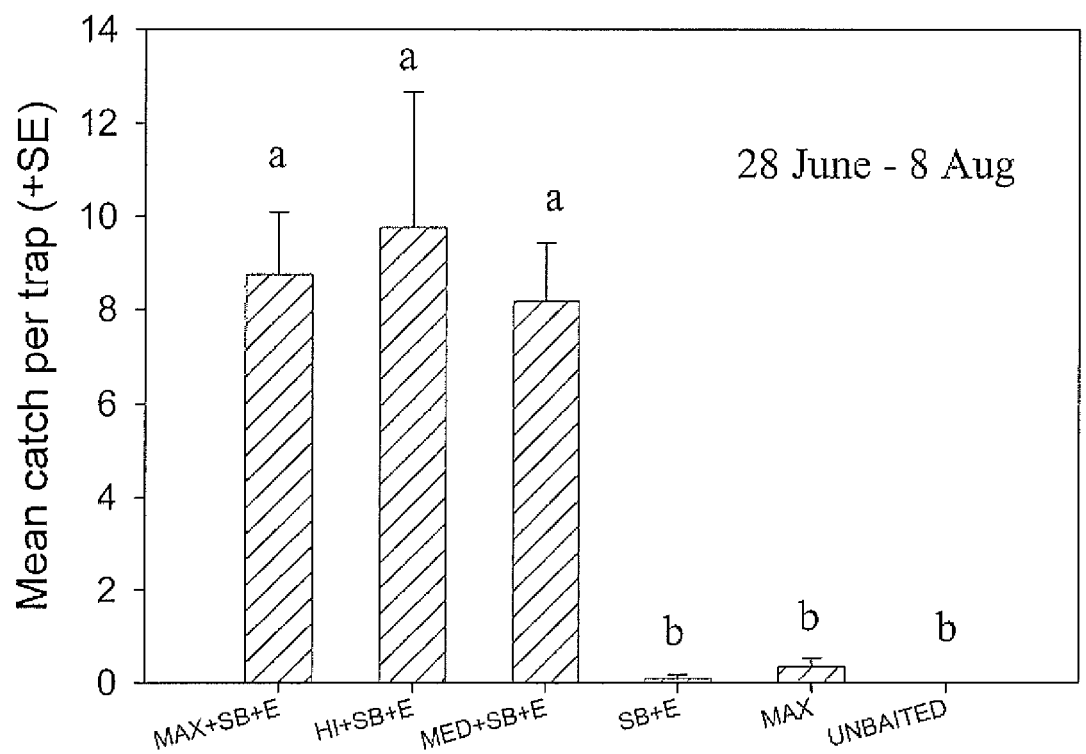
Figure 13:
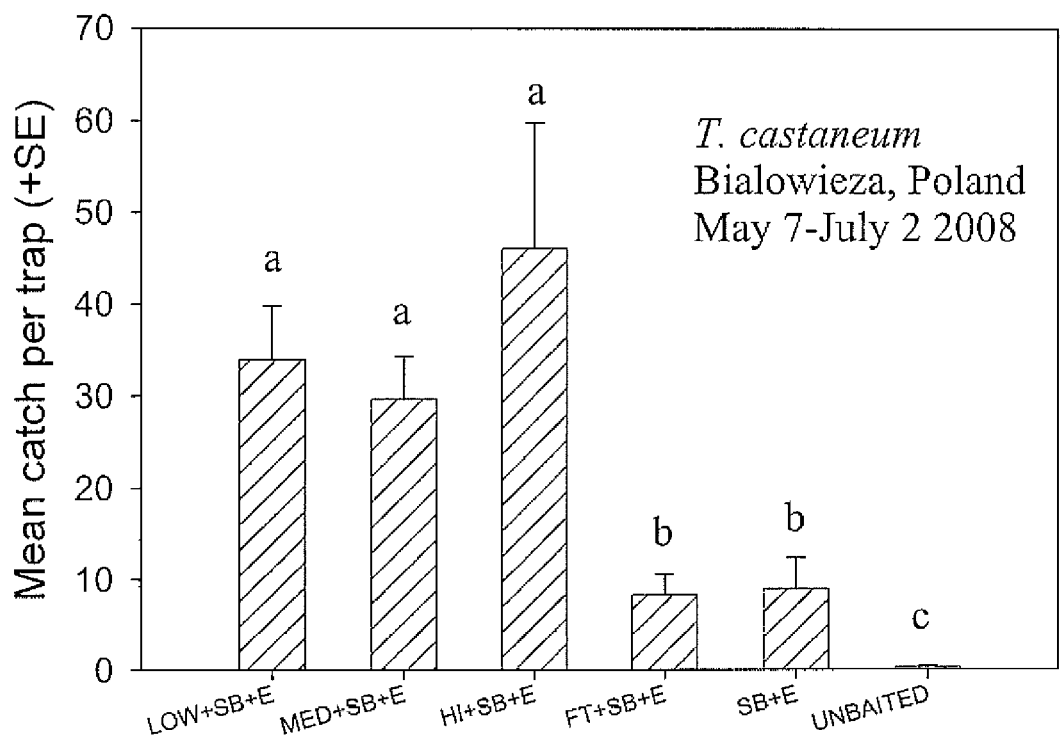
Figure 14:
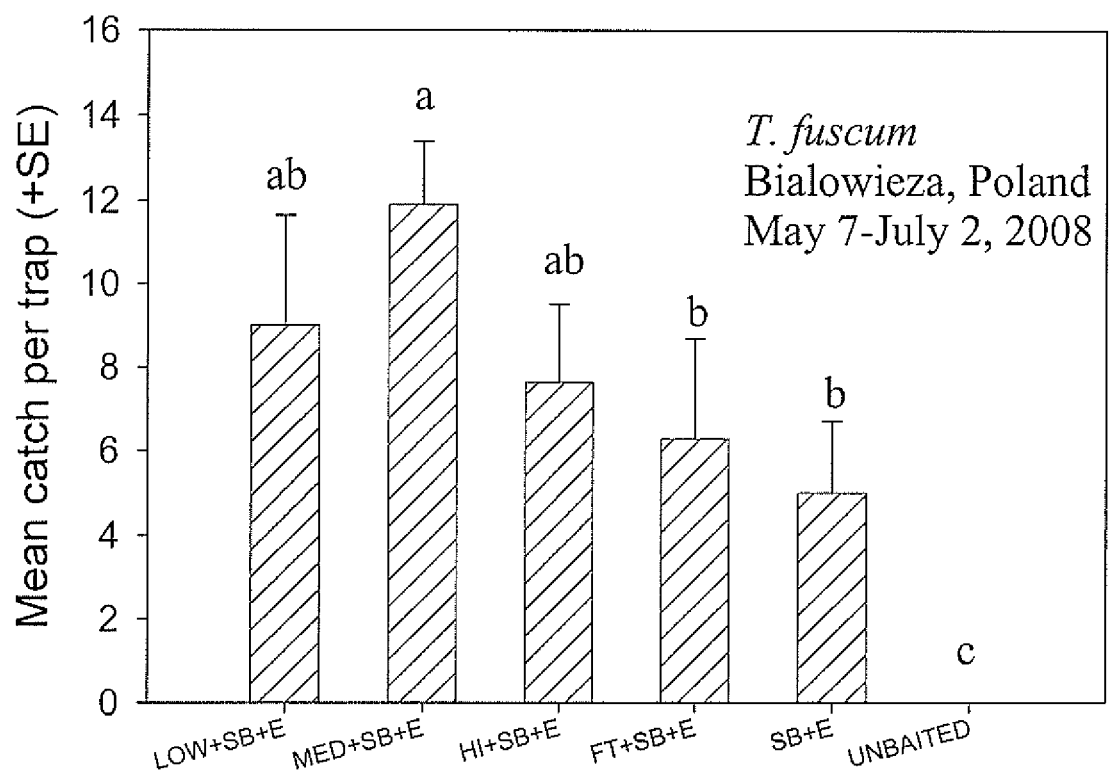
FIG. 14 Mean catch of *T. fuscum* in traps baited with low (1 mg/d), medium (4 mg/d) or high (32 mg/d) of racemic fuscumol plus spruce volatile (SB) and ethanol (E) lures. FT="fuscumate" or geranyl acetate, which did not boost catch compared to SB+E.

As will be appreciated by one of skill in the art, the conifer volatiles and the pheromone do not necessarily need to be mixed together. That is, the sources of the pheromone and the conifer volatiles may be separate but proximal to one another. As discussed above, it is the combination of the two that when emitted in the air acts as an attractant for *Tetropium*, for example, *Tetropium castaneum*, *Tetropium fuscum* and *Tetropium cinnamopterum*. In preferred embodiments, the attractant further comprises a source of ethanol, as discussed below. As will be appreciated by one of skill in the art, an 'effective amount' of (E)-6,10-dimethyl-5,9-undecadien-2-ol refers to an amount of (E)-6,10-dimethyl-5,9-undecadien-2-ol that is sufficient when added to or placed proximal to a source of conifer volatiles to produce a *Tetropium* attractant that attracts a statistically significantly greater amount of *Tetropium* insects than a source of conifer volatiles on its own or an amount of (E)-6,10-dimethyl-5,9-undecadien-2-ol that is sufficient when added to or placed proximal to a source of conifer volatiles and ethanol to produce a *Tetropium* attractant that attracts a statistically significantly greater amount of *Tetropium* insects than a source of conifer volatiles and ethanol alone. Effective release rates of fuscumol may range from 800 ug/d to 2000 ug/d (FIGS. 11, 12) or from 1 mg/d to 32 mg/d (FIGS. 13, 14). Specifically, as can be seen from FIGS. 13 and 14, fuscumate had no effect on attraction of either *T. fuscum* or *T. castaneum*. Furthermore, addition of any release rate of fuscumol to host volatile-baited traps significantly increased catch of *T. castaneum*.

According to another aspect of the invention ester derivatives of (E)-6,10-dimethyl-5,9-undecadien-2-ol are provided as novel compounds, as discussed herein.

According to another aspect of the invention, a method of attracting insects from the taxonomic groups *Tetropium castaneum*, *Tetropium fuscum* and *Tetropium cinnamopterum* is provided, comprising attracting insects from the taxonomic groups *Tetropium castaneum*, *Tetropium fuscum* or *Tetropium cinnamopterum* to a target by applying an effective amount of a attractant comprising a source of conifer volatiles and an effective amount of (E)-6,10-dimethyl-5,9-undecadien-2-ol or derivative thereof to said target.

According to yet another aspect of the invention, there is provided synthetic (E)-6,10-dimethyl-5,9-undecadien-2-ol and ester derivatives thereof as well as methods for producing same. As discussed herein, synthesis of racemic and optically enriched S-fuscumol was undertaken via the following approaches:
  (a) use of alkyl-CBS-oxazaborilidine catalysts to effect asymmetric reductions of prochiral ketones using for example borane adducts as reducing agents or other suitable reducing agents;
  (b) Chiral synthetic approaches beginning with chirally pure R- and S-lactate esters and copper catalyzed Grignard coupling to chiral lactyl alcohol tosylates;
  (c) Kinetic resolution of racemic secondary alcohols using a lipase (e.g. Novozyme 425) followed by chromatographic resolution and purification to obtain both R- and S-fuscumol simultaneously; and
  (d) Production of racemic fuscumol by borohydride or LAH reduction of geranyl acetone, shown in FIG. 5 and discussed below.

Figure 5:
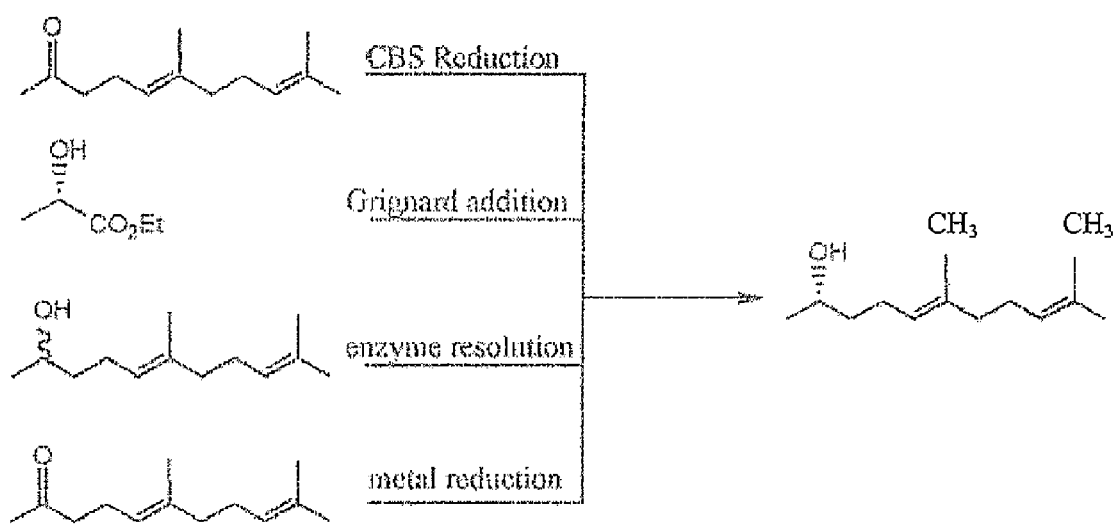
FIG. 5. Production of racemic fuscumol by borohydride or LAH reduction of geranyl acetone.

Exemplary synthesis schemes are summarized in FIGS. 5 and 6 and are discussed below. As will be apparent to one of skill in the art, a variety of other methods for synthesizing (E)-6,10-dimethyl-5,9-undecadien-2-ol may be developed using means known in the art.

In one embodiment of the invention, there is provided a method for synthesizing (E)-6,10-dimethyl-5,9-undecadien-2-ol comprising:
  dissolving E-(trans)-geranyl acetone in anhydrous tetrahydrofuran;
  cooling the mixture to 0° C. on ice;
  adding lithium aluminum hydride slowly while stirring the mixture;
  quenching the reaction by adding water drop wise;
  extracting the mixture with diethyl ether; and
  drying the extract over magnesium sulfate.

Lure Composition and Release Rates.

Spruce blend and ethanol lures were produced by PheroTech (Delta, British Columbia, Canada) and were stored at −18° C. until used in the field. The "spruce blend" lure comprises of a blend of racemic α-pinene, (−)-β-pinene, (+)-3-carene, (+)-limonene, and α-terpinolene at relative concentrations similar to those observed in cortical volatiles of *T. fuscum*-infested red spruce (Sweeney et al. 2004)[3]. As will be appreciated by one of skill in the art and as discussed above, other suitable 'spruce blends' or 'conifer volatiles' or 'spruce volatiles' as described above may be used within the invention. The spruce blend was released at ≈2,000 (one lure per trap) and 414 mg/d (207 mg/d per lure×2 lures per trap) from high and low release rate treatments, respectively, and 95% ethanol (Table 1). When ethanol is used alone, it is 95% purity as per Table 1, with a small amount of BITREX™ (denatonium benzoate) added to discourage vertebrate consumption. The terms "conifer volatiles" and the "host volatiles" as used elsewhere herein, also refer to the "spruce blend" mixture and in many cases in the examples refer to the spruce blend plus ethanol.

Materials and Methods

Adult *T. fuscum* and *T. cinnamopterum* were reared from bolts (35 cm long×20-40 cm diam.) cut from infested white or red spruce in Halifax, NS, and incubated at 20-22° C. and 45%-60% RH in a containment facility at the Atlantic Forestry Centre (AFC). Beetle emergence was checked 5 d per week for 12 weeks. *Tetropium* adults were identified to species (Smith and Humble 2000)[2], separated by sex, and stored individually, unfed, in glass vials at 3-4° C. until used. Volatiles were collected separately from male and female *T. fuscum* and *T. cinnamopterum* by drawing air through activated charcoal, then through a glass chamber (2.8 cm diam.×18 cm long) containing 5-6 beetles, and then through 200 mg of pre-cleaned PORAPAK®Q (chromatography beads) (Waters Associates, Inc.), using a vacuum line and a flow rate of 250-300 mL/min. Two 9 cm diam. circles of filter paper were inserted in each glass chamber; one piece lined the inside of the chamber to provide better footing for the beetles, and the other was pleated to provide niches and separate individuals. Beetles were acclimatized to room conditions (20-22° C., 40%-60% RH, 15:9 (L:D) cycle)) for 24 h before volatile collection. Beetles were not provided food or water. We aerated a total of four samples of *T. fuscum* males, two samples each of *T. fuscum* females and *T. cinnamopterum* males, and one sample of *T. cinnamopterum* females. Mean (+SE) age (days since eclosion, stored at 3-4° C.) of *Tetropium* adults was 17.3 (2.4). Volatiles were collected for 24-96 h per replicate. The glass chambers and lines were cleaned between each replicate and the activated charcoal was replaced every second replicate. The inside of the glass chambers was rinsed with dichloromethane and the PORAPAK®Q (chromatography beads) eluted with methylene chloride (3×3 mls) to capture any volatiles and the extracts analyzed separately by gas chromatography/mass spectrometry (GC/MS) on a Hewlett-Packard 5890 GC and a 5971 mass selective detector in the electron impact (EI) mode. The column used for analysis was a Supelco SPB-5 capillary (30 m×0.32 mm×0.25 μm film) in the splitless mode with helium as carrier gas. The injection port was at 220° C. and the oven temperature was programmed from 70° C., held for 3 min and then increased at 15° C./min to 220° C. and held for 15 min. Mean daily release rate of pheromone per beetle was estimated by dividing the total amount of pheromone collected per replicate by the number of beetles in the chamber and number of days the volatiles were collected.

Extracts (cal male equivalent in hexane) and synthetics (30 ng fuscumol) were tested for antennal stimulation of *T. fuscum* and *T. cinnamopterum* males and females using an electroantennogram (EAG) system and EAG/GC-EAD signal recording (IDAC-232) and analysis software v.2.6 (SYNTECH, The Netherlands). Antennae from males and females were excised close to the head and used intact with SPECTRA-60™ gel (electrode gel) (Parker, USA) for electrical contact.

Extracts (ca.1 male equivalent in hexane) and synthetics (30 ng fuscumol) were tested for antennal stimulation of *T. fuscum* and *T. cinnamopterum* males and females using an electroantennogram (EAG) system and EAG/GC-EAD signal recording (IDAC-232) and analysis software v.2.6 (SYNTECH, The Netherlands). Antennae from males and females were excised close to the head and used intact with Spectra©-60 gel (Parker, USA) for electrical contact.

Synthetic (racemic) fuscumol (>99% pure; GC/MS) was made by lithium aluminum hydride (LAH) reduction of geranyl acetone (Aldrich) and the structural assignment of this secondary alcohol was verified by EI mass spectral and $^1$H NMR analysis. Oxidation of natural pheromone was performed with pyridinium chlorochromate (PCC) in hexane/dichloromethane (50/50).

The synthetic pheromone, alone and in combination with host volatile attractants, was tested in a field experiment on McNabs Island, Halifax, Nova Scotia, from 5 Jul. to 29 Aug. 2006, using COLOSSUS TRAPS™ (insect traps) (PheroTech Inc. Delta, British Columbia) (Sweeney et al. 2006)[4]. Unbaited traps and traps baited with host volatiles alone served as controls, for a total of four treatments. Treatments were replicated 15 times in a randomized complete block design with 30 m between traps and blocks. Each trap was suspended from a rope tied between two conifers separated by at least 2 m, with the collecting bucket 10-20 cm above the ground. To retain captured beetles, the bucket contained a 50:50 mixture of propylene glycol and deionized water plus 0.5 mL/L of Kodak Photo-Flo 200 and 12.5 mg/L of BITREX® (denatonium benzoate) (Macfarlan Smith, Edinburgh). Pheromone was dispensed at ca. initially 800 µg/d dropping to 50 µg/d over a 4 week period (determined by weight loss at 23° C.) from a polymerase chain reaction (PCR) sample tube (Axygen Scientific Inc., CA) (0.2-mL thick) with a 1 mm diam. hole drilled in the cap. Each lure contained ca. 15 mg of synthetic pheromone. Host volatiles were dispensed from two ultra high release rate (UHR) lures, one containing *T. fuscum* kairomone (a blend of five monoterpenes released at about 2000 mg/d (Sweeney et al. 2006=spruce blend))[4], and one containing ethanol released at 275 mg/d (PheroTech Inc., Delta, British Columbia). The host volatile lures have a field life of about 90 d at 21-24° C., so were not replaced for the 8-week duration of the experiment. The pheromone lures were replaced every 4 weeks. Traps were checked weekly and specimens preserved in 70% ethanol. All *Tetropium* spp. were identified to species and sex and voucher specimens retained at AFC. We deleted catch in all treatments in block 18 (week of 19-26 July) and block 23 (week of 26 July-2 August) from the season totals due to trap disturbance. Data for total catch per trap were transformed by either log (y+1) or square root, depending on which produced residuals that fit the normal distribution (Shapiro and Wilk test) (Zar 1999)[9] using SAS PROC Univariate (SAS Institute 1999-2001), and subjected to ANOVA separately for each species and sex. Paired t-tests were used to compare catch of males vs. females within species. Sex ratio (males+1/females+1) was compared among treatments within species for all traps with non-zero catch using ANOVA. Means were compared using the Ryan-Einot-Gabriel-Walsh multiple range test (SAS Institute 1999-2001).

Results

Figure 2:
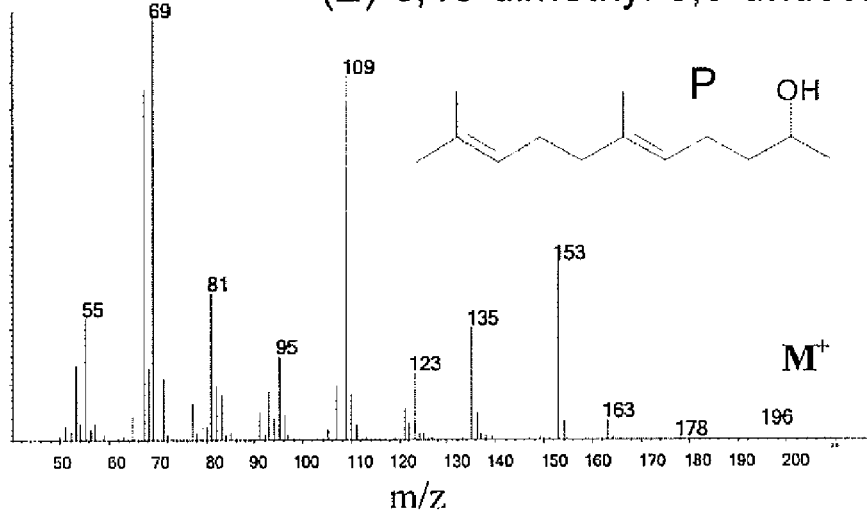
FIG. 2. Mass spectra of the pheromone component (E-6, 10-dimethyl-5,9-undecadienol-2-of (geranyl acetol) produced by male *T. fuscum* (a) and of its oxidation product geranyl acetone (b)
Figure 2:
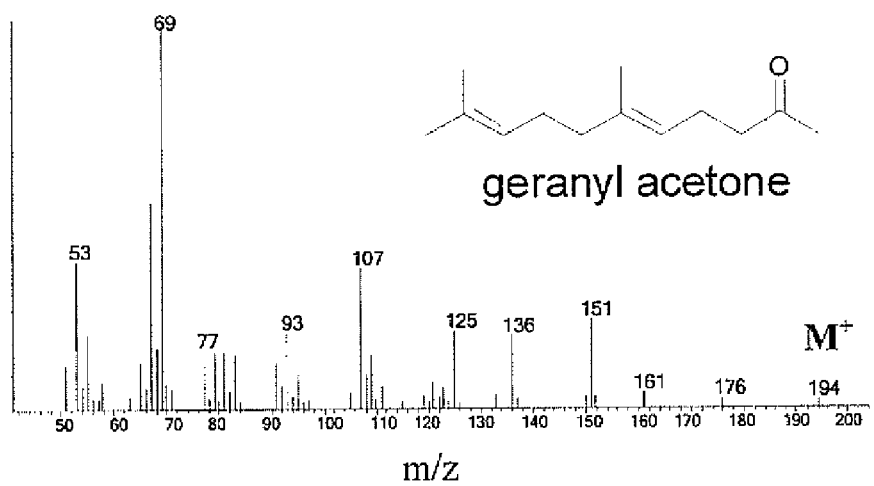

The GC profile of volatiles collected from *T. fuscum* males and females and *T. cinnamopterum* males consistently revealed a major component (P) emitted by males of both species (FIGS. 1a,b) but not by females of either species. (*T. fuscum* females shown, FIG. 1c). The EI mass spectrum (FIG. 2a) identified this compound (P) (comparison of the natural spectrum with The NIST mass spectral database and authentic standards) as the homoterpenoid (E)-6,10-dimethyl-5,9-undecadien-2-ol ($M^+$ 196 amu; geranyl acetol), which as discussed above we name "fuscumol." The compound was identical in its mass spectrum and retention time to the product obtained by LAH reduction of authentic geranyl acetone. PCC oxidation of the natural mixture taken from a PORAPAK®Q extract, generated geranyl acetone (EI mass spectrum; $M^+$ 194 amu; FIG. 2b) and was identical to authentic geranyl acetone as evidenced by EI mass spectra and retention time data. No trace of the 5Z isomer (neryl acetol, from LAH reduction of neryl acetone, Aldrich), which elutes 0.3 minutes earlier (baseline resolved) under these conditions than 5E, was detected. Release rates were estimated as ca. 480-720 ng/d/male for *T. fuscum* and 120-240 ng/d/male for *T. cinnamopterum*. In EAG puffs (ca. 30 ng source concentration), racemic fuscumol elicited 2-3 times greater antennal response in females (6.05+0.3 mV, *T. fuscum* and 1.7+0.2 mV, *T. cinnamopterum*; n=5) than males of both species.

Figure 3:
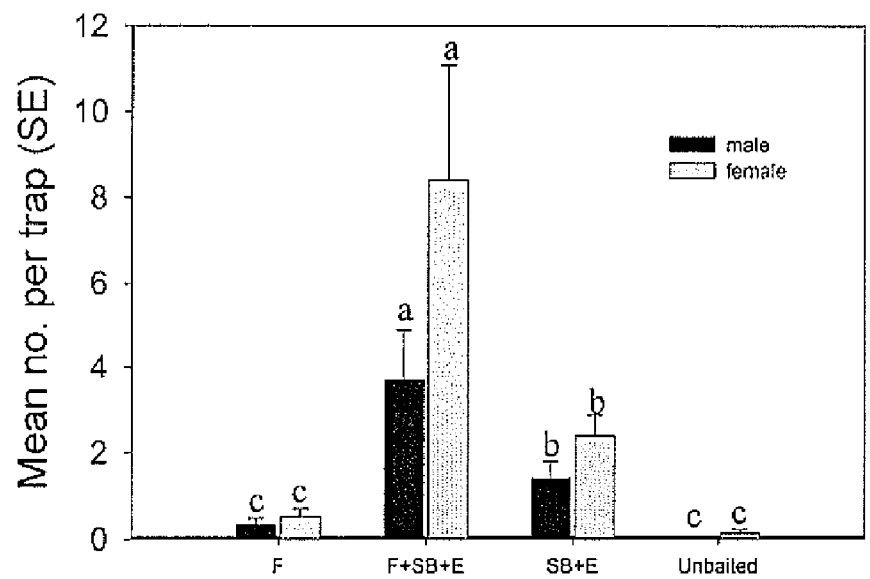
FIG. 3. Mean number (+SE) of male and female *T. fuscum* (a) and *T. cinnamopterum* (b) captured in COLOSSUS TRAPS™ (insect traps) baited with synthetic pheromone candidate (P), host volatile lures (HV), P plus host volatiles (P+HV), or un-baited traps, over the entire 8-week trapping period. Within each space and sex, means with the same letters were not significantly different (ANOVA and Ryan-Einot-Gabriel-Walsh range test, a=0.05). Data for *T. fuscum* males and females and *T. cinnamopterum* females were transformed by log (y+1); data for the catch of *T. cinnamopterum* males were transformed by square root.
Figure 3:
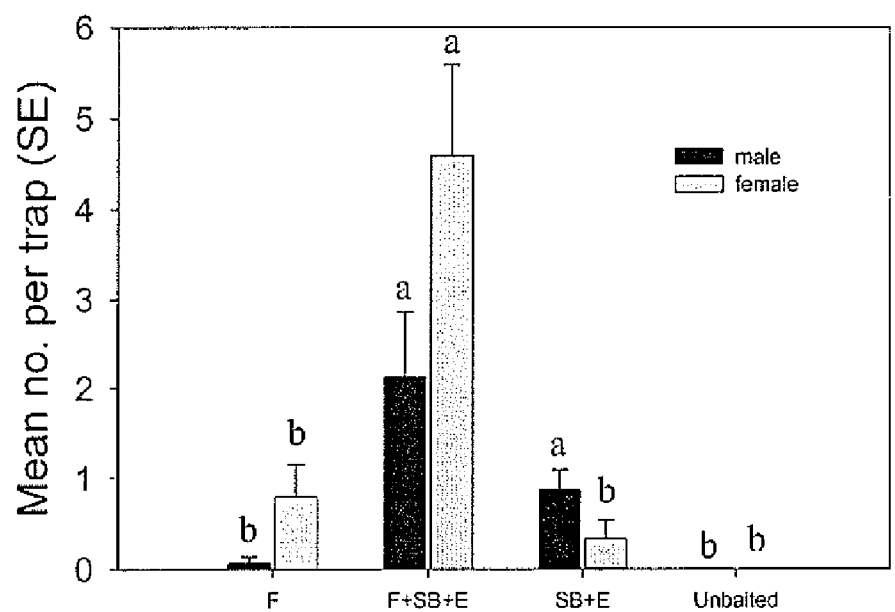

Traps baited with synthetic fuscumol plus host volatiles caught significantly more female and male *T. fuscum* (FIG. 3a) and female *T. cinnamopterum* (FIG. 3b) than traps baited with host volatiles alone, or unbaited traps. Catch in traps baited with fuscumol alone did not differ from that in unbaited traps. Overall, about twice as many females as males were captured for both species (paired t-tests, P<0.01) but the sex ratio did not differ significantly among treatments for *T. fuscum* (F=0.42; df=3,20; P=0.73). Sex ratio of *T. cinnamopterum* differed significantly among treatments (F=8.1; df=2,13; P=0.005) being male biased in traps baited with host volatiles only and female biased in traps baited with fuscumol or fuscumol plus host volatiles.

As discussed above, also described herein are a plurality of methods for the synthesis of fuscumol. As will be appreciated by one of skill in the art, other suitable methods for preparation of synthetic fuscumol may be used or developed using means known in the art.

Racemic Fuscumol Synthesis.

Figure 6:
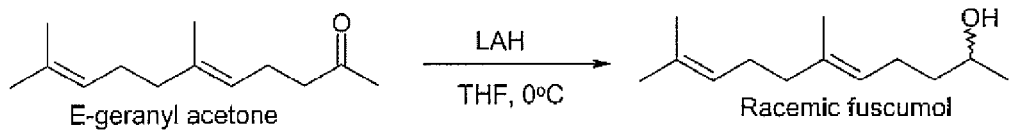
FIG. 6. Fuscumol synthesis schemes.
Figure 6:
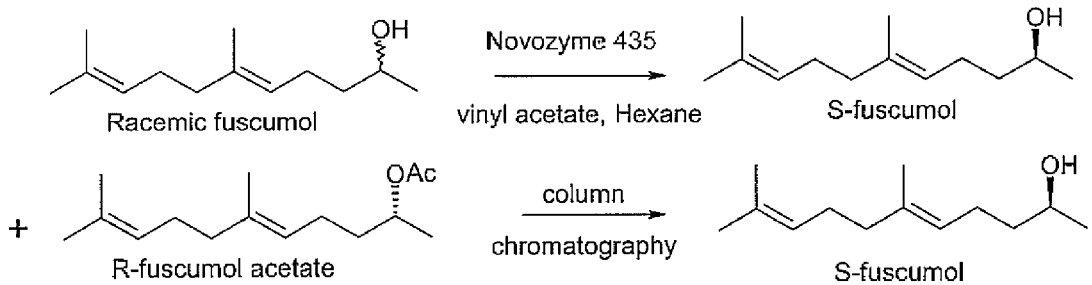
Figure 6:
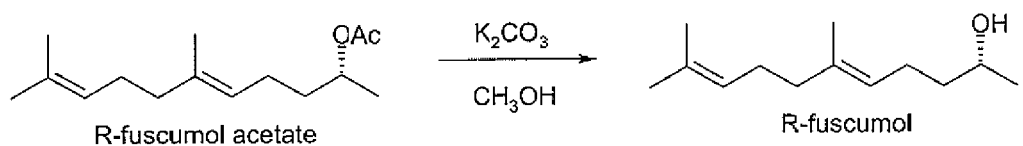
Figure 6:
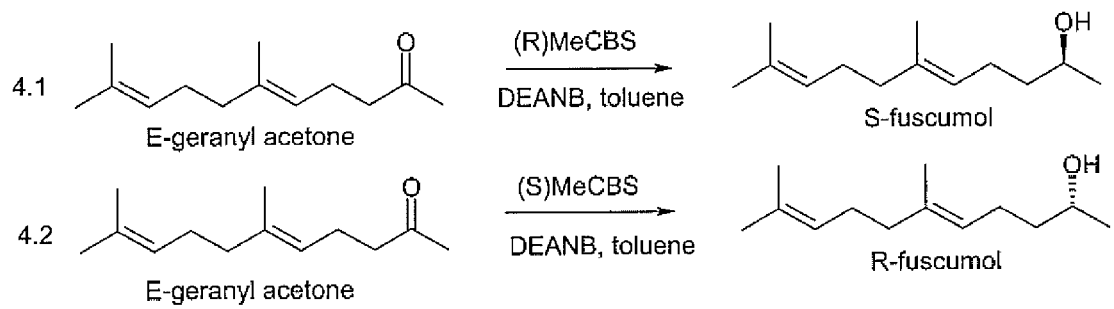
Figure 6:
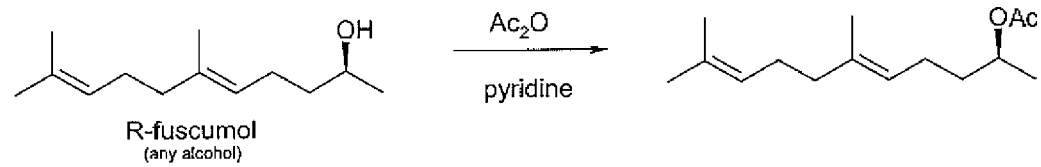
Figure 7:
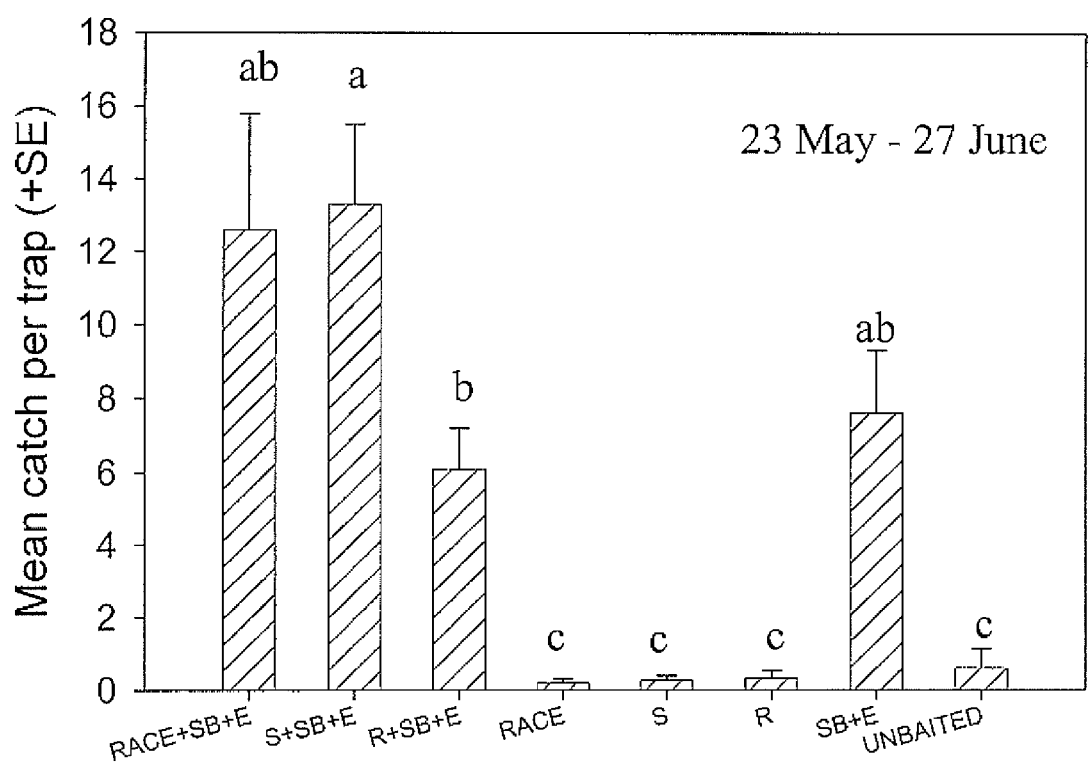
FIGS. 7 and 8 show capture of *T. fuscum* and *T. cinnamopterum* in COLOSSUS TRAPS™ (insect traps) baited with different enantiomers of fuscumol (S, R, racemic blend) with and without host volatiles: RACE+SB+E=racemic fuscumol+spruce blend+ethanol; S+SB+E=S-fuscumol+spruce blend+ethanol; R+SB+E=R-fuscumol+spruce blend+ethanol; SB+E=spruce blend+ethanol; RACE=racemic fuscumol; S=S-fuscumol; R=R-fuscumol; and unbaited.
Figure 8:
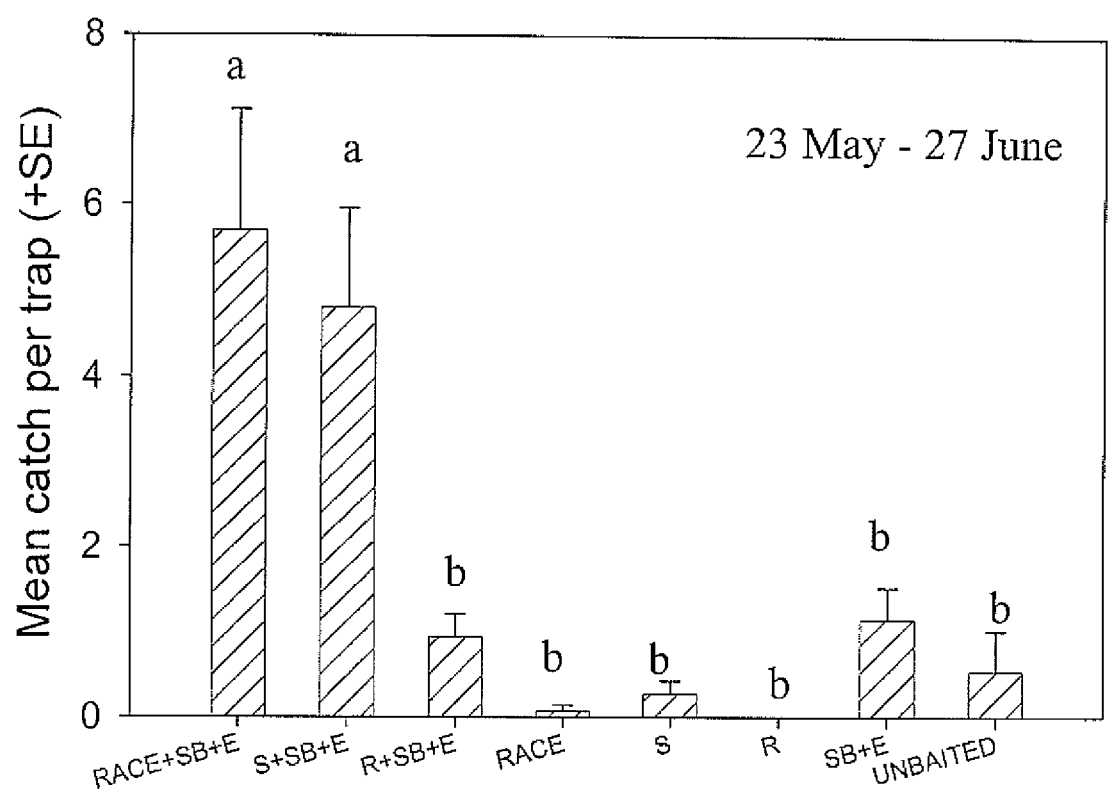
Figure 10:
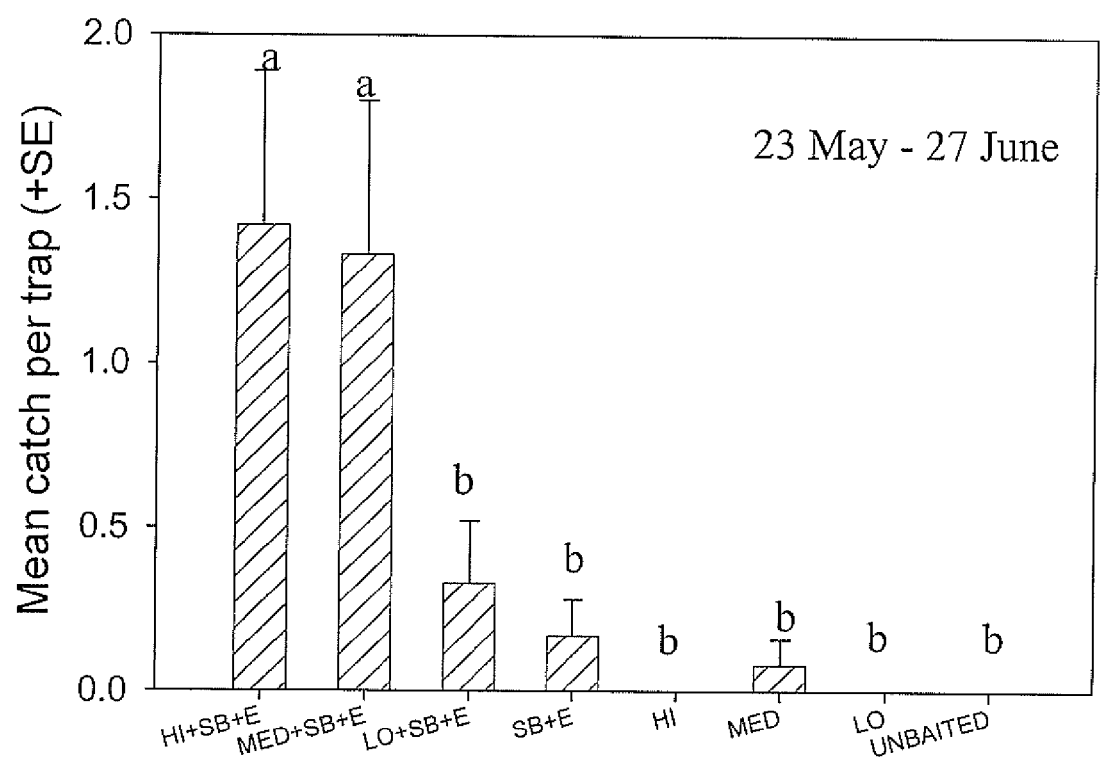

This is outlined in Scheme 1 of FIG. 6. E-(trans)-geranyl acetone (1 g), is dissolved in 10 ml anhydrous THF (tetrahydrofuran) and cooled to 0° C. in ice. LAH (lithium aluminum hydride) (0.26 g) is added slowly with stirring and the reaction mixture is stirred for 2 hours and quenched by adding water drop wise. The reaction mixture is then extracted with diethyl ether (3×10 ml) and dried over magnesium sulfate, the ether removed in vacuo to give racemic fuscumol in ca 95% yield. The EI-mass spectrum indicates full reduction of the ketone to the secondary alcohol, fuscumol with only a trace of E-geranyl acetone remaining (see FIGS. 1 and 2 for spectral data). Treatment of racemic fuscumol with S-acetly lactyl chloride (pyridine catalyzed) and analysis by GC/MS on a 30 m SPB-5 capillary column (70-220° C. @ 15/minute) indicates a 50/50 mixture (racemic) of both R and S-diastereomers, the S-isomer eluting last.

Similar diastereomer formation with insect-derived material from both *T. fuscum* and *T. cinnamopterum* showed that fuscumol had the S-configuration in both species with <1% of the R-enantiomer present. The generic ketone and analogue-acetate, could not be detected in either species. *Tetropium castaneum* in Poland, a potential invasive species to North America, has also been found to be attracted by either racemic or S-fuscumol in the presence of host volatiles and ethanol.

Chiral Syntheses of S- and R-Fuscumol Using Lipase

Enantioselective syntheses of these compounds is outlined in Schemes 2 & 3, shown in FIG. 6. An immobilized lipase enzyme from *Candida antarctica* (Sigma; Novozyme® 435; 10,000 units/g), ca.50 mg, was added to a stirred solution of racemic fuscumol and 0.5 g of vinyl acetate as acylating agent (Gries et al., 2006)[10] in 3 ml hexane The solution is stirred for 5 hours at 40° C., the resin filtered off, solvents removed in vacuo, and alcohol (S) and acetate (R) separated by flash chromatography. This afforded an approx 80% yield with ca 99% ee (optical rotation+2.4 (neat); reported+3.4, Madyastha and Gururaja, 1994[11] allowing assignment of the absolute configuration of this product as (S) of the S-fuscumol directly as determined by diastereomer formation and GC/MS as before. (Scheme 2). The R-enantiomer was obtained in ca 50% yield (98% ee) by acetate group removal after stirring with potassium carbonate (Scheme 3) and the usual workup. Esters (acetates, propionates, butyrates, etc.) of any of the alcohols, racemic or enantiomerically pure, were readily prepared e.g. acetates by acetylation using pyridine-catalyzed treatment with acetic anhydride and the conventional workup (Scheme 5).

Chiral Syntheses of S- and R-Fuscumol Using Asymmetric Reduction Catalysts: Oxazaborolidines.

The asymmetric reduction of prochiral E-geranyl acetone was accomplished using N, N-diethylaniline-borane as the borane source and commercially available MeCBS catalysts as outlined in Schemes 4.1 and 4.2, shown in FIG. 6, with (R)Me CBS catalyst producing the S-fuscumol enantiomer in 99% yield and 87% ee and the (S)MeCBS catalyst producing the R-fuscumol in 74% yield and 80% ee (Salunkhe & Burkhardt, 1997)[12]. It is of note that further enantiomeric enrichment can be achieved with the lipase if desired.

Referring to FIGS. 7-12, Low, medium, high, and "max" release rates corresponded to 15 mg of fuscumol in an Eppendorf tube that was were sealed (low), sealed with a 1 mm hole in the cap (medium), sealed with a 2.5 mm hole in the cap (high), and with the cap open (max).

The low release rate lures with sealed caps probably release an order of magnitude less fuscumol, e.g., about 800-1000 ng/d as opposed to 800 ug/d for the medium lures. The high lures with 2.5 mm diam openings appear to release at a markedly greater rate than 800 ug/d, but the "max" lures with open caps do not seem to differ much in release rate from the High lures.

Attraction of *Tetropium fuscum* (F.) and *Tetropium castaneum* (L.) to Pheromone and Host Volatiles.

Trapping experiments were run in 2007 in Halifax, NS, and Bialowieża, Poland to test the response of *Tetropium* species to fuscumol, a sex pheromone emitted by male *Tetropium fuscum* (F.) and male *T. cinnamopterum*. In 2006 in Halifax, NS, a racemic (50/50 S/R) blend of synthetic fuscumol was found to significantly increase mean trap catch of male and female *T. fuscum* and female *T. cinnamopterum* when combined with spruce host volatile lures (monoterpene blend plus ethanol) (Silk et al. 2007)[9]. Male *T. fuscum* emit primarily S-fuscumol so we hypothesized that a synthetic lure of pure S-fuscumol would be more attractive than pure R-fuscumol, and possibly more attractive than racemic fuscumol, especially if R-fuscumol was the major pheromone component of a sympatric sibling species such as *T. castaneum*. The ultimate objective was to determine if we could improve the efficacy of the lure for use in applications for survey and control of *T. fuscum*. Conducting the experiment in Poland allowed us to test the response of a different population of *T. fuscum* from that in Halifax and also to determine the attraction of the pheromone lures to another potentially invasive species, *T. castaneum*.

There were eight different lure treatments: S-fuscumol; R-fuscumol; racemic fuscumol; S-fuscumol+UHR (ultra high release rate) spruce blend lure+UHR ethanol lure; R-fuscumol+UHR spruce blend lure+UHR ethanol lure; racemic fuscumol+UHR spruce blend lure+UHR ethanol lure; UHR spruce blend lure+UHR ethanol lure; and unbaited controls.

On McNabs Island near Halifax, NS, COLOSSUS TRAPS™ (insect traps) were used with 15 replicates per treatment and in Bialowieża, APT (Advanced Pheromone Technologies) INTERCEPT TRAPS™ (insect traps) were used with 9 replicates per treatment. The treatments were laid out in randomized complete block designs with 30 m spacing between traps. Traps were out from 15 May to 27 Jun. 2007 on McNabs Island and from 30 Apr. to 25 Jun. 2007 in Bialowieża. Data for total catch per trap of each target species were subjected to ANOVA using SAS GLM (SAS Institute 1999-2001) and means were compared with the Ryan-Einot-Gabriel-Welsh range test. Residuals were tested for departure from normality using the Shapiro-Wilk test (SAS PROC Univariate) (Zar 1999)[7] and when necessary data were transformed by log (x+1).

Figure 4:
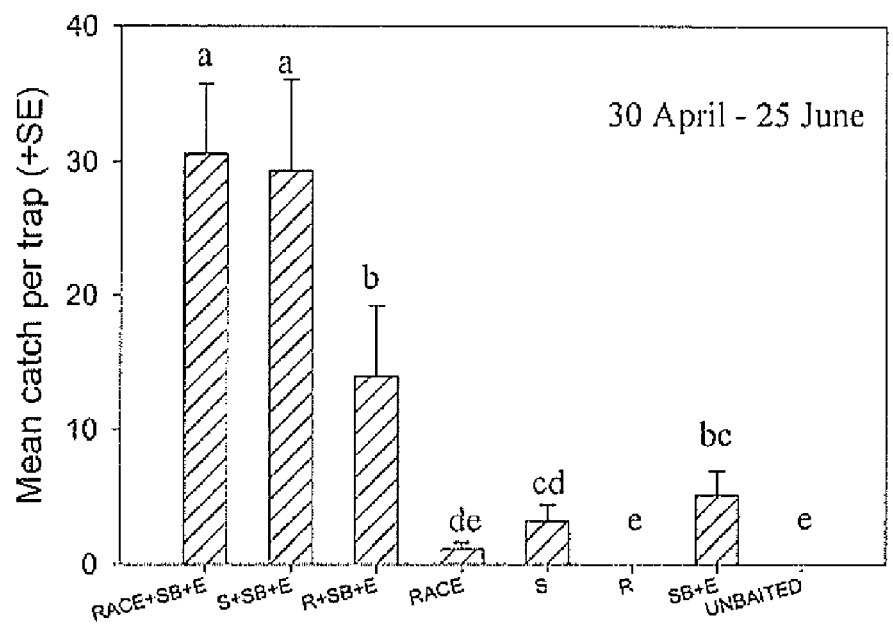
FIG. 4. Mean catch of a. *Tetropium fuscum* and b. *T. castaneum* in APT INTERCEPT TRAPS™ (insect traps) baited with synthetic fuscumol (pure S—, pure R—, or racemic) alone and combined with host volatile lures (SB=spruce blend, a blend of monoterpenes in an ultra high release rate (UHR) lure; E=ethanol in an UHR lure) in Bialowieza, Poland in 2007. Means with different letters differ significantly (ANOVA and REGW range test on data transformed by log (x+1), P<0.05).
Figure 4:
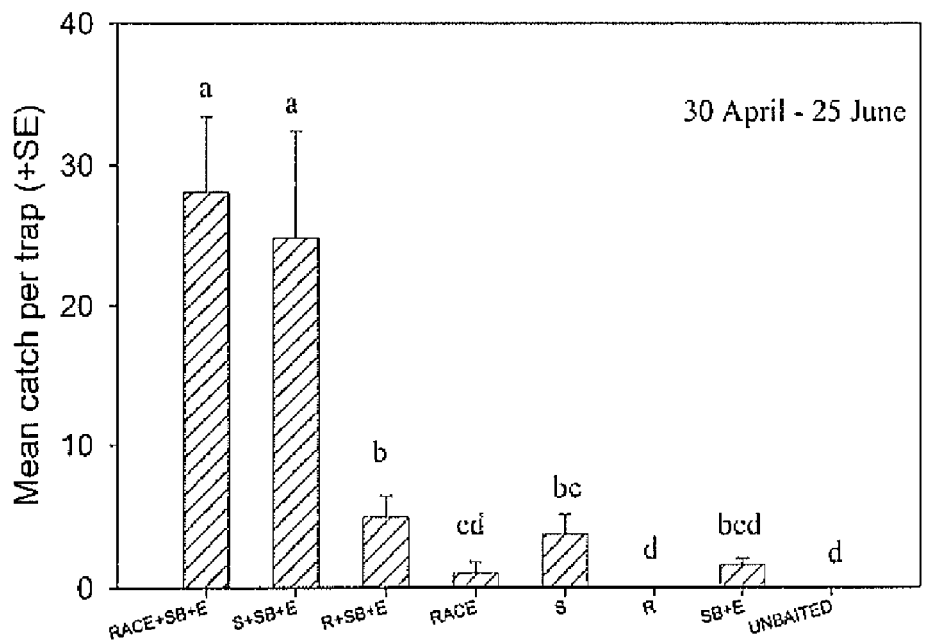

Biatowieża. As predicted, S-fuscumol was significantly more attractive to *T. fuscum* than R-fuscumol or an unbaited trap but did not differ significantly in mean catch from racemic fuscumol. Without the host volatile lures, mean catch of *T. fuscum* was low for both S- and racemic fuscumol (1-3 beetles per trap) (FIG. 4a). The combination of spruce blend and ethanol with either S-fuscumol or racemic fuscumol boosted mean catch of *T. fuscum* 10× compared to the pheromone alone and 6× compared to the host volatiles alone. These results confirm our earlier results and indicate that the racemic fuscumol+spruce blend and ethanol lure used operational surveys should be significantly better at detecting the presence of *T. fuscum* than the host volatile lures alone. The data also suggest that attraction of *T. fuscum* to S-fuscumol is not reduced by the presence of R-fuscumol. This is good news cost-wise because racemic fuscumol is much cheaper to produce than chirally pure S-fuscumol. The relatively low mean catch in traps baited with spruce blend plus ethanol suggest that competition occurred among the treatments, i.e., the more attractive traps baited with racemic fuscumol plus spruce blend and ethanol may have drawn *Tetropium* adults away from less attractive treatments. Since traps were spaced about 30 m apart this suggests that lures were drawing beetles from more than 15 m away.

Results for *T. castaneum* were very similar to those for *T. fuscum* (FIG. 4b). In fact, the numbers of *T. fuscum* captured per trap was significantly correlated with the numbers of *T. castaneum* captured per trap, across all treatments (r=0.83, P<0.0001). This was surprising since one would predict these sympatric species would use different pheromones or pheromone blends as a means of reproductive isolation. This suggests that S-fuscumol is not the only component in the sex pheromones of these species or that reproductive isolation is controlled by close range (e.g. contact) pheromones or post-mating mechanisms. One of the few differences was that mean catch in traps baited with spruce blend plus ethanol was not significantly different to that in unbaited traps for *T. castaneum* (FIG. 4b) but was so for *T. fuscum*. In the same area of the Bialowieża forest in 2006, a mean of 40 *T. castaneum* were captured in intercept traps baited with spruce blend and ethanol. The large drop in catch in host volatile baited traps in 2007 may be due to competition from traps baited with pheromone plus host volatiles.

While the preferred embodiments of the invention have been described above, it will be recognized and understood that various modifications may be made therein, and the appended claims are intended to cover all such modifications which may fall within the spirit and scope of the invention.

REFERENCES CITED

1. Smith G, Hurley J E (2000) First North American record of the Palearctic species *Tetropium fuscum* (Fabricius) (Coleoptera: Cerambycidae). Coleopt Bull 54:540.

2. Smith G, Humble L M (2000) The brown spruce longhorn beetle. Exotic Forest Pest Advisory 5. Natural Resources Canada, Canadian Forest Service. 4 p.
3. Sweeney J, de Groot P, MacDonald L, Smith S, Cocquempot C, Kenis M, Gutowski J (2004) Host volatile attractants for detection of *Tetropium fuscum* (F.), *Tetropium castaneum* (L.), and other longhorned beetles (Coleoptera: Cerambycidae). Environ Entomol 33:844-854.
4. Sweeney J, Gutowski J M, Price J, and de Groot P (2006) Effect of semiochemical release rate, killing agent, and trap design on detection of *Tetropium fuscum* (F.) and other longhorn beetles (Coleoptera: Cerambycidae). Environ Entomol 35:645-654.
5. Allison J D, Borden J H, Seybold S J (2004) A review of the chemical ecology of the Cerambycidae (Coleoptera). Chemoecology 14:123-150.
6. Lacey E S, Ginzel M D, Millar J G, Hanks L M (2004) Male-produced aggregation pheromone of the cerambycid beetle *Neoclytus acuminatus acuminatus*. J Chem Ecol 30:1493-1507.
7. Zar J H (1999) Biostatistical Analysis. 4th Ed. Prentice-Hall, Inc., Upper Saddle River, N.J. 663 p.
8. Landolt P J, Phillips T W (1997) Host plant influences on sex pheromone behavior of phytophagous insects. Annu Rev Entomol 42:371-391.
9. Silk P J, J Sweeney, Wu J, J Price, J Gutowski, E G Kettela. 2007. Evidence for a male-produced pheromone in *Tetropium fuscum* (F.) and *Tetropium cinnamopterum* (Kirby) (Coleoptera: Cerambycidae), Naturissenschaften. 94:697-701.
10. Gries R, G Khaskin, H Daroogheh, C Mart, S Karadag, M Kubilay Er, R Britton, G Gries. 2006. (2S,12Z)-2-Acetoxy-12-heptadecene: Major Sex pheromone Component of Pistachio Twig Borer, *Kermania pistaciella*, J Chem Ecol., 32:2667-2677.
11. Madyastha, K M, Gururaja T L. 1994. Asymmetric Reduction of Prochiral Ketones by Cell-Free systems from *Atcaligenes eutrophus*. J. Chem. Tech. Biotechnol.59: 249-255.
12. Salunke A M, Burkhardt, E R. 1997. Highly Enantioselective Reduction of Prochiral Ketones with N,N-diethylaniline-borane (DEANB) in Oxazaborolidine-catalysed Reductions. Tetrahedron Letters. 38: 1523-1526.

TABLE 1

Composition, purity, and average release rate of lures tested for attraction of *T. fuscum* and other cerambycid beetles in field trapping bioassays in Halifax, Nova Scotia and Bialewieźa, Poland, 2002-2004

| Lure | Component | Percentage of lure composition | Purity (%) | High release lures | Low release lures |
|---|---|---|---|---|---|
| Spruce blend[b] | Racemic α-pinene | 44 | 97 | 2,000 | 207 |
| | (−)-β-Pinene | 10 | 98 | | |
| | (+)-β-Carene | 10 | 93 | | |
| | (+)-Limonene | 18 | 99 | | |
| | α-Terpinolene | 9 | 92 | | |
| Ethanol | Ethanol | 100 | 95 | 275 | 30 |

Mean release rate (mg/d at 20° C.)[a]

[a]Data provided by PheroTech.
[b]Release rate not determined for individual components.

TABLE 2

Sex ratio: both sexes attracted but usually more females captured than males

| | Percent Males | |
|---|---|---|
| Experiment | F + SB + E | SB + E |
| Chiral - NS | 50 | 60* |
| Chiral - PD | 42* | 44 |
| Release 1 | 39* | 43 |
| Release 2 | 28* | 37 |

*paired t-test, P < 0.05
55% males in reared *T. fuscum*

The invention claimed is:

1. An insect attractant comprising a source of conifer volatiles, ethanol and an effective amount of (2S,5E)-6,10-dimethyl-5,9-undecadien-2-ol or derivatives thereof.

2. The insect attractant according to claim 1 wherein the insect is a *Tetropium*.

3. The insect attractant according to claim 1 wherein the insect is selected from the group consisting of: *Tetropium castaneum*, *Tetropium fuscum* and *Tetropium cinnamopterum*.

4. A method of attracting insects from the taxononic groups *Tetropium castaneum*, *Tetropium fuscum* and *Tetropium cinnamopterum* to a target comprising:
    attracting insects from the taxonomic groups *Tetropium castaneum*, *Tetropium fuscum* or *Tetropium cinnamopterum* to a target by applying an effective amount of a attractant comprising a source of conifer volatiles and an effective amount of (E)-6,10-dimethyl-5,9-undecadien-2-ol or derivative thereof to said target.

5. The method according to claim 4 wherein the attractant includes ethanol.

6. The method according to claim 4 wherein the (E)-6,10-dimethyl-5,9-undecadien-2-ol is a racemic mix of (E)-6,10-dimethyl-5,9-undecadien-2-ol.

7. The method according to claim 4 wherein the (E)-6,10-dimethyl-5,9-undecadien-2-ol is substantially pure S-chiral form of (E)-6,10-dimethyl-5,9-undecadien-2-ol.

8. A method for synthesizing (E)-6,10-dimethyl-5,9-undecadien-2-ol comprising:
    dissolving E-(trans)-geranyl acetone in anhydrous tetrahydrofuran;
    cooling the mixture to 0° C. on ice;
    adding lithium aluminium hydride slowly while stirring the mixture;
    quenching the reaction by adding water dropwise;
    extracting the mixture with diethyl ether; and
    drying the extract over magnesium sulfate.

* * * * *